(12) United States Patent
Dent et al.

(10) Patent No.: US 8,937,211 B2
(45) Date of Patent: Jan. 20, 2015

(54) ABSORBENT ARTICLES COMPRISING LOW BASIS WEIGHT FILMS EXHIBITING LOW GLUE BURN THROUGH

(75) Inventors: Terra Louise Dent, Mason, OH (US); Joseph Leslie Grolmes, Madeira, OH (US); Jeffrey Richard Holley, Mason, OH (US); Yoshihiko Tachibana, Loveland, OH (US); Terrill Alan Young, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1052 days.

(21) Appl. No.: 12/133,404

(22) Filed: Jun. 5, 2008

(65) Prior Publication Data

US 2008/0306463 A1    Dec. 11, 2008

Related U.S. Application Data

(60) Provisional application No. 60/933,205, filed on Jun. 5, 2007.

(51) Int. Cl.
*A61F 13/15* (2006.01)
*C08J 5/18* (2006.01)

(52) U.S. Cl.
CPC . *A61F 13/15* (2013.01); *C08J 5/18* (2013.01); *A61F 2013/15016* (2013.01); *C08J 2323/10* (2013.01)
USPC ............................ 604/367; 604/370; 604/372

(58) Field of Classification Search
USPC ......................................... 604/367, 370, 372
See application file for complete search history.

(56) References Cited

U.S. PATENT DOCUMENTS

| | | | |
|---|---|---|---|
| 3,563,243 A | 2/1971 | Lindquist | |
| 3,639,199 A * | 2/1972 | Brandts et al. | 428/110 |
| 3,860,003 A | 1/1975 | Buell | |
| 3,911,173 A | 10/1975 | Sprague, Jr. | |
| 3,929,135 A | 12/1975 | Thompson | |
| 4,275,105 A * | 6/1981 | Boyd et al. | 428/198 |
| 4,324,246 A | 4/1982 | Mullane et al. | |
| 4,342,314 A | 8/1982 | Radel et al. | |
| 4,463,045 A | 7/1984 | Ahr et al. | |
| 4,472,328 A | 9/1984 | Sugimoto et al. | |
| 4,554,297 A | 11/1985 | Dabi | |
| 4,573,986 A | 3/1986 | Minetola et al. | |
| 4,609,518 A | 9/1986 | Curro et al. | |
| 4,610,678 A | 9/1986 | Weisman et al. | |
| 4,629,643 A | 12/1986 | Curro et al. | |

(Continued)

FOREIGN PATENT DOCUMENTS

| | | | |
|---|---|---|---|
| DE | 2004 042 405 A1 | 3/2006 | |
| EP | 0 492 942 B2 | 2/2000 | |

(Continued)

OTHER PUBLICATIONS

International Search Report, mailed Oct. 21, 2008, PCT/IB2008/052225.

*Primary Examiner* — Lynne Anderson
(74) *Attorney, Agent, or Firm* — Sarah M. DeCristofaro; Laura L. Whitmer

(57) ABSTRACT

Low basis weight films having a heat capacity×density value of greater than about 970,000 $Ws/m^3K$, as measured by the method described herein, the films having a basis weight of less than about 16 gsm and comprising at least about 10% polypropylene.

6 Claims, 1 Drawing Sheet

(56) References Cited

U.S. PATENT DOCUMENTS

| | | |
|---|---|---|
| 4,636,207 A | 1/1987 | Buell |
| 4,673,402 A | 6/1987 | Weisman et al. |
| 4,695,278 A | 9/1987 | Lawson |
| 4,704,115 A | 11/1987 | Buell |
| 4,740,520 A | 4/1988 | Hallenbach et al. |
| 4,785,996 A | 11/1988 | Ziecker et al. |
| 4,795,454 A | 1/1989 | Dragoo |
| 4,808,178 A | 2/1989 | Aziz et al. |
| 4,834,735 A | 5/1989 | Alemany et al. |
| 4,842,666 A | 6/1989 | Werenicz |
| 4,888,231 A | 12/1989 | Angstadt |
| 4,892,536 A | 1/1990 | DesMarais et al. |
| 4,900,317 A | 2/1990 | Buell |
| 4,909,803 A | 3/1990 | Aziz et al. |
| 4,940,464 A | 7/1990 | Van Gompel et al. |
| 4,950,254 A | 8/1990 | Andersen et al. |
| 4,988,344 A | 1/1991 | Reising et al. |
| 4,988,345 A | 1/1991 | Reising |
| 4,990,147 A | 2/1991 | Freeland |
| 5,006,394 A | 4/1991 | Baird |
| 5,037,416 A | 8/1991 | Allen et al. |
| 5,085,654 A | 2/1992 | Buell |
| 5,092,861 A | 3/1992 | Nomura et al. |
| 5,147,345 A | 9/1992 | Young et al. |
| 5,234,423 A | 8/1993 | Alemany et al. |
| 5,246,433 A | 9/1993 | Hasse et al. |
| 5,260,345 A | 11/1993 | DesMarais et al. |
| 5,269,775 A | 12/1993 | Freeland et al. |
| 5,342,338 A | 8/1994 | Roe |
| 5,492,751 A | 2/1996 | Butt, Sr. et al. |
| 5,507,760 A | 4/1996 | Wynne et al. |
| 5,569,234 A | 10/1996 | Buell et al. |
| H1630 H | 1/1997 | Roe et al. |
| 5,607,760 A | 3/1997 | Roe |
| 5,609,587 A | 3/1997 | Roe |
| 5,628,097 A | 5/1997 | Benson et al. |
| 5,635,191 A | 6/1997 | Roe et al. |
| H1670 H | 7/1997 | Aziz et al. |
| 5,643,588 A | 7/1997 | Roe et al. |
| 5,681,301 A * | 10/1997 | Yang et al. ............ 604/370 |
| 5,769,838 A | 6/1998 | Buell et al. |
| 5,897,545 A | 4/1999 | Kline et al. |
| 5,899,895 A | 5/1999 | Robles et al. |
| 5,899,896 A | 5/1999 | Suprise et al. |
| 5,916,661 A | 6/1999 | Benson et al. |
| 5,941,864 A | 8/1999 | Roe |
| 5,957,908 A | 9/1999 | Kline et al. |
| 5,968,025 A | 10/1999 | Roe et al. |
| 6,107,539 A | 8/2000 | Palumbo et al. |
| 6,118,041 A | 9/2000 | Roe et al. |
| 6,120,487 A | 9/2000 | Ashton |
| 6,120,489 A | 9/2000 | Johnson et al. |
| 6,414,215 B1 | 7/2002 | Roe |
| 6,476,288 B1 | 11/2002 | VanRijswijck et al. |
| 6,545,197 B1 | 4/2003 | Muller et al. |
| 6,627,787 B1 | 9/2003 | Roe et al. |
| 6,680,422 B2 | 1/2004 | Roe |
| 6,909,028 B1 * | 6/2005 | Shawver et al. ............ 604/370 |
| 7,378,566 B2 * | 5/2008 | Soerens et al. ............ 604/365 |
| 2002/0017376 A1 | 2/2002 | Geltser et al. |
| 2003/0190339 A1 | 10/2003 | Skover et al. |
| 2003/0233082 A1 | 12/2003 | Kline et al. |
| 2004/0122398 A1* | 6/2004 | Schnabel et al. ......... 604/385.01 |
| 2007/0254158 A1 | 11/2007 | Bormann et al. |
| 2008/0015531 A1* | 1/2008 | Hird et al. ............ 604/367 |
| 2008/0131681 A1 | 6/2008 | Bormann et al. |
| 2008/0310075 A1 | 12/2008 | Takeoka et al. |

FOREIGN PATENT DOCUMENTS

| | | |
|---|---|---|
| WO | WO 95/24173 | 9/1995 |
| WO | WO 00/69382 | 11/2000 |

* cited by examiner

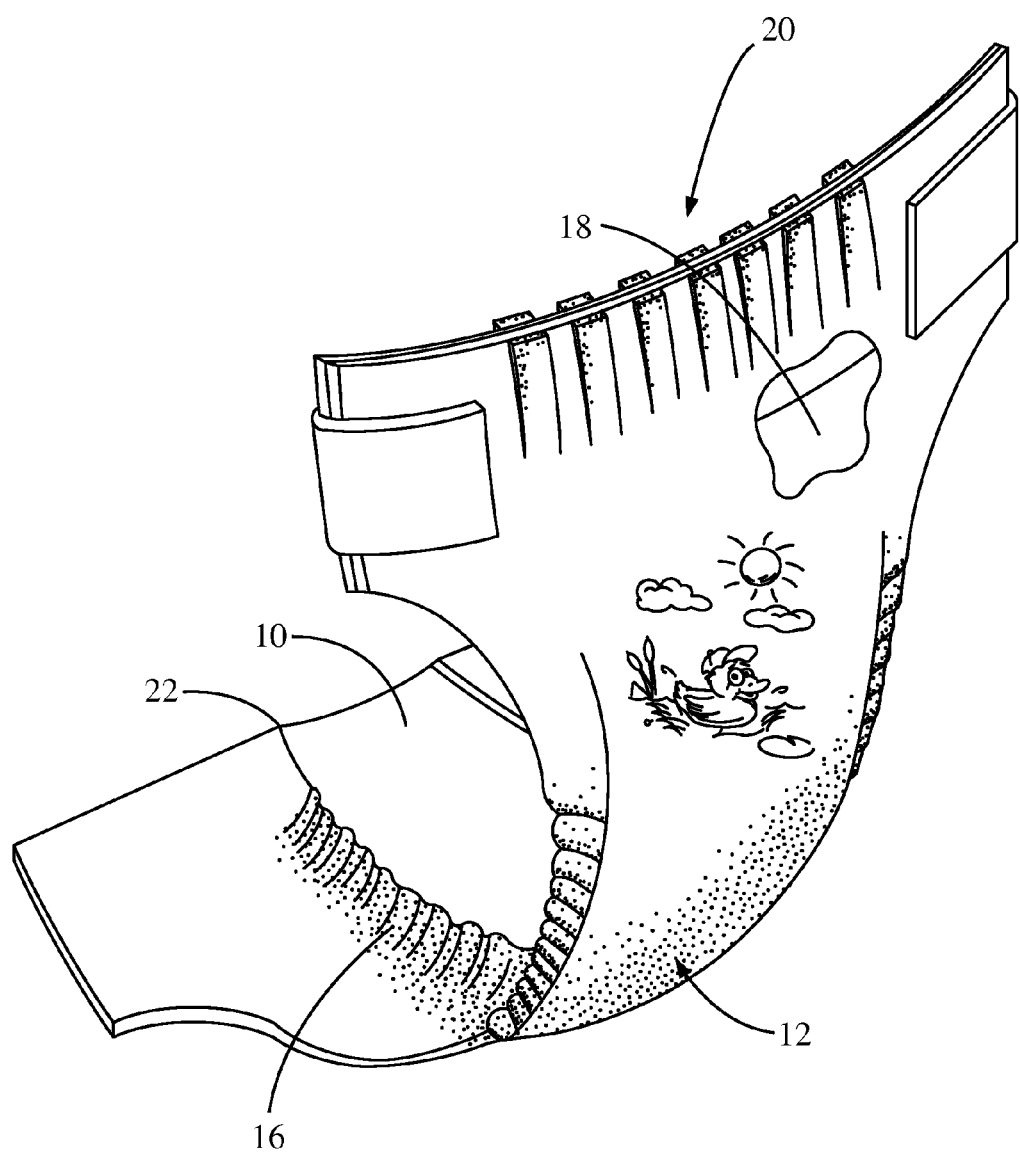

ABSORBENT ARTICLES COMPRISING LOW BASIS WEIGHT FILMS EXHIBITING LOW GLUE BURN THROUGH

CROSS REFERENCE TO RELATED APPLICATIONS

This application claims the benefit of U.S. Provisional Application No. 60/933,205, filed on Jun. 5, 2007.

FIELD OF THE INVENTION

The present invention relates to absorbent articles comprising low basis weight films exhibiting low glue burn through. Specifically, the low basis weight films of the present invention include polypropylene to help achieve low glue burn through, as determined by the method described herein.

BACKGROUND OF THE INVENTION

Low film basis weights may increase a film's thermal sensitivity to hot melt systems. As a result, the risk of hot melt adhesives burning through the film increases. Glue burn through (GBT) occurs when the hot glue partially or completely melts the polymeric film in an area so that the thickness of the polymer is reduced or no longer exists. Glue burn through can occur by two different mechanisms: instantaneous melting or mechanical pressure. Instantaneous melting occurs when the film melts instantaneously when the hot adhesive contacts the web, usually resulting in contamination severe enough to tear the film web. When glue burn through occurs from the mechanical pressure mechanism, the glue and film are in contact and the area goes under a mechanical nip. The mechanical nip applies pressure to the area where the soft film pores collapse or forces the glue through the film. Glue burn through can potentially impact the product by eliminating or weakening the film structure or altering the opaqueness of the film. Thus, the film is diminished in performance (may cause leakage from pinholes or thermal melting), integrity (could tear easily), and appearance (looks plastic/cheap or consumer perceives it as product failure).

Higher basis weight films typically do not exhibit glue burn through. However, higher basis weight films are more expensive than lower basis weight films. Conversely, lower basis weight films are less expensive than higher basis weight films, but many lower basis weight films exhibit glue burn through. Thus, a need exists for a lower basis weight film that exhibit lower glue burn through.

SUMMARY OF THE INVENTION

The present invention provides for a low basis weight film that does not exhibit glue burn through. The low basis weight films of the present invention have a heat capacity×density value of greater than about 970,000 Ws/m$^3$K, as measured by the method described herein. The films of the present invention have a basis weight of less than about 16 gsm, and the film comprises a polymeric resin that comprises at least about 10% polypropylene. The low basis weight films of the present invention may be used in absorbent articles.

BRIEF DESCRIPTION OF THE DRAWINGS

FIG. 1 is a perspective view of an article made according to the present invention.

DETAILED DESCRIPTION OF THE INVENTION

As used herein, the following terms have the following meanings:

As used herein, the term "absorbent articles" refers to devices that absorb and contain body exudates, and, more specifically, refers to devices that are placed against or in proximity to the body of the wearer to absorb and contain the various exudates discharged from the body. Absorbent articles may include diapers, training pants, adult incontinence undergarments, feminine hygiene products, breast pads, care mats, bibs, wound dressing products, and the like. As used herein, the term "body fluids" or "body exudates" includes, but is not limited to, urine, blood, vaginal discharges, breast milk, sweat and fecal matter.

As used herein, the term "absorbent core" refers to the component of the absorbent article that is primarily responsible for fluid handling properties of the article, including acquiring, transporting, distributing and storing body fluids. As such, the absorbent core typically does not include the topsheet, backsheet or outer cover of the absorbent article.

As used herein, the term "bonded" refers to different materials being attached (cohesively or adhesively) in at least a portion thereof. The attached portions may be random or may have a pattern such as stripes, spirals, dots, and the like. The attached portions may be located at the peripheries, throughout the surface area, or both. Suitable attachment means known in the art may be used, including but not limited to adhesives, heat, pressure, crimping, ultrasonic, chemical (via hydrogen bonds or other cohesive forces), mechanical (e.g., fasteners, entanglements), hydraulic, vacuum and combinations thereof.

As used herein, the term "diaper" refers to an absorbent article generally worn by infants and incontinent persons about the lower torso so as to encircle the waist and legs of the wearer and that is specifically adapted to receive and contain urinary and fecal waste. As used herein, term "diaper" also includes "pants" which is defined below.

As used herein, the term "disposable" is used in its ordinary sense to mean an article that is disposed or discarded after a limited number of usage events over varying lengths of time, preferably less than about 20 events, more preferably less than about 10 events, even more preferably less than about 5 events, and most preferably less than about 2 events.

As used herein, the term "joined" encompasses configurations wherein an element is directly secured to the other element by affixing the element directly to the other element, and configurations wherein the element is indirectly secured to the other element by affixing the element to intermediate member(s), which in turn are affixed to the other element.

The term "longitudinal" refers to a direction running from a waist edge to an opposing waist edge of the article and generally parallel to the maximum linear dimension of the article. Directions within ±45° of the longitudinal direction are considered to be "longitudinal".

The term "lateral" refers to a direction running from a side edge to an opposing side edge of the article and generally at a right angle to the longitudinal direction and in the same plane as the longitudinal direction. Directions within ±45° of the lateral direction are considered to be "lateral".

As used herein, the term "nonwoven" refers to a web that has a structure of individual fibers which are interlaid forming a matrix, but not in an identifiable repeating manner. Nonwoven webs may be formed by a variety of processes known to those skilled in the art, for example, meltblowing, spunbonding, wet-laying, air-laying, and various bonding-carding processes.

The terms "pant" or "training pant", as used herein, refer to disposable garments having a waist opening and leg openings designed for infant or adult wearers. A pant may be placed in position on the wearer by inserting the wearer's legs into the leg openings and sliding the pant into position about a wearer's lower torso. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened). While the terms "pant" or "pants" are used herein, pants are also commonly referred to as "closed diapers", "prefastened diapers", "pull-on diapers", "training pants" and "diaper-pants". Suitable pants are disclosed in U.S. Pat. No. 5,246,433, issued to Hasse, et al. on Sep. 21, 1993; U.S. Pat. No. 5,569,234, issued to Buell et al. on Oct. 29, 1996; U.S. Pat. No. 6,120,487, issued to Ashton on Sep. 19, 2000; U.S. Pat. No. 6,120,489, issued to Johnson et al. on Sep. 19, 2000; U.S. Pat. No. 4,940,464, issued to Van Gompel et al. on Jul. 10, 1990; U.S. Pat. No. 5,092,861, issued to Nomura et al. on Mar. 3, 1992; U.S. Patent Publication No. 2003/0233082 A1, entitled "Highly Flexible And Low Deformation Fastening Device", filed on Jun. 13, 2002; U.S. Pat. No. 5,897,545, issued to Kline et al. on Apr. 27, 1999; U.S. Pat. No. 5,957,908, issued to Kline et al on Sep. 28, 1999.

As used herein, the term "region" refers to a zone or an area comprising a material being physically, chemically, or visually distinguishable from surrounding or adjoining materials. Various regions of materials may include transitional regions in between. The regions may be positioned in the z-dimension or in the xy-dimension. As used herein, the term "z-dimension" refers to the dimension orthogonal to the length and width of the structure or article. The z-dimension usually corresponds to the thickness of the structure or article. As used herein, the term "xy-dimension" refers to the plane orthogonal to the thickness of the member, core or article when the member, core or article is in a flat-out state. The xy-dimension usually corresponds to the length and width, respectively, of the structure or article in a flat-out state.

Absorbent Articles

FIG. 1 depicts the absorbent articles of the present invention, e.g., diaper(s) 20, which comprise a liquid pervious topsheet 10, a backsheet 12 that is at least partially joined to the topsheet 10, an absorbent core 18 disposed at least partially between the topsheet 10 and the backsheet 12, a first cuff 16 along a longitudinal edge 22 of the topsheet 10. In certain embodiments, the absorbent articles may additionally include one or more components selected from the group consisting of an outer cover, side panels, an elastic feature, a fastening system, and combinations thereof.

An outer cover (which may comprise the backsheet) forms the chassis, onto which other components of the diaper are added to form the unitary structure of the diaper. In alternative embodiments, the article may be preformed by the manufacturer to create a pant. The term "pant", as used herein, refers to disposable garments having a waist opening and leg openings designed for infant or adult wearers. A pant may be placed in position on the wearer by inserting the wearer's legs into the leg openings and sliding the pant into position about the wearer's lower torso. A pant may be preformed by any suitable technique including, but not limited to, joining together portions of the article using refastenable and/or non-refastenable bonds (e.g., seam, weld, adhesive, cohesive bond, fastener, etc.). While the term "pant" is used herein, pants are also commonly referred to as "closed diapers", "prefastened diapers", "pull-on diapers", "training pants" and "diaper-pants". Suitable pants are disclosed in U.S. Pat. Nos. 5,246,433; 5,569,234, 6,120,487, 6,120,489, 4,940,464, 5,092,861, 5,897,545, 5,957,908, and U.S. Patent Publication 2003/0233082A1.

The absorbent articles of the present invention comprise a topsheet 10. The topsheet is preferably compliant, soft feeling, and non-irritating to the wearer's skin. It can be elastically stretchable in one or two directions. The topsheet has at least one longitudinal edge 22 and in most instances has two. Further, the topsheet is liquid pervious, permitting liquids (e.g., menses, urine, and/or runny feces) to readily penetrate through its thickness. A suitable topsheet can be manufactured from a wide range of materials such as woven and nonwoven materials; apertured or hydroformed thermoplastic films; porous foams; reticulated foams; reticulated thermoplastic films; and thermoplastic scrims. Suitable woven and nonwoven materials may comprise of natural fibers such as wood or cotton fibers; synthetic fibers such as polyester, polypropylene, or polyethylene fibers; or combinations thereof. If the topsheet includes fibers, the fibers may be spunbond, carded, wet-laid, meltblown, hydroentangled, or otherwise processed as is known in the art. One suitable topsheet comprising a web of staple-length polypropylene fibers is manufactured by Veratec, Inc., a Division of International Paper Company, of Walpole, Mass. under the designation P-8.

Preferred topsheet for use in the present invention are selected from high loft nonwoven topsheets and apertured film topsheet. Apertured film topsheet typically are pervious to bodily exudates, yet non-absorbent, and have a reduced tendency to allow fluids to pass back through and rewet the wearer's skin. Suitable apertured films include those described in U.S. Pat. Nos. 5,628,097, 5,916,661, 6,545,197, 6,107,539, and PCT Patent Publication WO 00/69382 A2.

Further, suitable topsheet materials for depositing solid excretions thereon may include nonwovens having apertures, which are at least in the portions that are aligned with the feces deposition region of the article. Suitable apertured nonwovens are described in more detail in U.S. Pat. Nos. 6,414,215, 5,342,338, and 5,941,864 and U.S. Patent Publication 2002/017376. In another embodiment of feces handling articles, such topsheets can be combined with feces handling members, e.g., underlying such topsheets, and which are further described in the abovementioned patent documents.

Suitable formed film topsheets are described in U.S. Pat. Nos. 3,929,135, 4,324,246, 4,342,314, 4,463,045, 5,006,394. Other suitable topsheets may be made in accordance with U.S. Pat. Nos. 4,609,518 and 4,629,643. Such formed films are available from The Procter & Gamble Company of Cincinnati, Ohio as "DRI-WEAVE" and from Tredegar Corporation, based in Richmond, Va., as "CLIFF-T."

Preferably, at least a portion of the topsheet is made of a hydrophobic material or is treated to be hydrophobic in order to isolate the wearer's skin from liquids contained in the absorbent core. If the topsheet is made of a hydrophobic material, preferably at least a portion of the upper surface of the topsheet is treated to be hydrophilic so that liquids will transfer through the topsheet more rapidly. The topsheet can be rendered hydrophilic by treating it with a surfactant or by incorporating a surfactant into the topsheet. Suitable methods for treating the topsheet with a surfactant include spraying the topsheet material with the surfactant and/or immersing the material into the surfactant. A more detailed discussion of such a treatment and hydrophilicity is contained in U.S. Pat. Nos. 4,988,344, 4,988,345, and 4,950,254. A more detailed discussion of some suitable methods for incorporating a surfactant in the topsheet 24 can be found in U.S. Statutory Invention Registration No. H1670. Alternatively, the topsheet may include an apertured web or film which is hydrophobic. This may be accomplished by eliminating the hydrophilizing treatment step from the production process and/or applying a hydrophobic treatment to the topsheet, such as a polytetraflouroethylene compound like SCOTCHGUARD or a hydrophobic lotion composition, as described below. In such embodiments, it is preferred that the apertures be large enough to allow the penetration of aqueous fluids like urine without significant resistance.

Any portion of the topsheet may be coated with a lotion as is known in the art. Examples of suitable lotions include those described in U.S. Pat. Nos. 5,607,760, 5,609,587, 5,635,191, 5,643,588, and 5,9680,25. The lotion may function alone or in combination with another agent as the hydrophobizing treatment described above. The topsheet may also include or be treated with antibacterial agents, some examples of which are disclosed in PCT Publication No. WO 95/24173. Further, the topsheet, the outer cover or any portion of the topsheet or outer cover may be embossed and/or matte finished to provide a more cloth like appearance.

The topsheet may comprise one or more apertures to ease penetration of exudates therethrough, such as urine and/or feces (solid, semi-solid, or liquid). The size of at least the primary aperture is important in achieving the desired waste encapsulation performance. If the primary aperture is too small, the waste may not pass through the aperture, either due to poor alignment of the waste source and the aperture location or due to fecal masses having a diameter greater than the aperture. If the aperture is too large, the area of skin that may be contaminated by "rewet" (from the article) is increased. Typically, the aperture should have an area of between about 10 cm$^2$ and about 50 cm$^2$. The aperture preferably has an area of between about 15 cm$^2$ and 35 cm$^2$.

Further, the topsheet may be fully or partially elasticated or may be foreshortened so as to provide a void space between the topsheet and the core. Exemplary structures including elasticized or foreshortened topsheets are described in more detail in U.S. Pat. Nos. 4,892,536, 4,990,147, 5,037,416, and 5,269,775.

The absorbent article further comprises a first cuff 16 along a longitudinal edge 22 of the topsheet 10. This first cuff 16 is useful for providing improved containment of liquids and other body exudates. First cuffs 16 may also be referred to as outer leg cuff, leg bands, side flaps, leg cuffs or elasticized cuffs. U.S. Pat. No. 3,860,003 describes a disposable diaper which provides a contractible leg opening having a side flap and one or more elastic members to provide an elasticized leg cuff.

The first cuff 16 may be constructed in a number of different configurations, including those described in U.S. Pat. Nos. 3,860,003, 4,636,207, 4,695,278, 4,704,115, 4,795,454, 4,900,317, 4,909,803 (Reissued as USRE34920), 5,085,654, 5,492,751, 6,476,288 and SIR H1630.

Additionally, an absorbent article of the present invention may include one or more second cuffs that also provide improved containment of liquids and other body exudates. Second cuffs may also be referred to as barrier leg cuffs, inner leg cuffs or "stand-up" elasticized flaps. U.S. Pat. Nos. 4,808,178 and 4,909,803 (Reissued as USRE34920) describe disposable diapers having "stand-up" elasticized flaps that improve the containment of the leg regions.

First cuff and second cuff may both be provided by way of a dual cuff, as exampled in U.S. Pat. Nos. 4,695,278 and 4,795,454. Additional cuffs may be provided in an article of the present invention as detailed in US Statutory Invention Registration H1630.

The backsheet 12 may or may not be impervious to fluids (e.g., menses, urine, and/or runny feces). Accordingly, one embodiment of the backsheet is manufactured from a thin plastic film, although other flexible liquid impervious or pervious materials may also be used. As used herein, the term "flexible" refers to materials which are compliant and will readily conform to the general shape and contours of the human body. The backsheet 12 prevents the exudates absorbed and contained in the absorbent core from wetting articles which contact the absorbent article such as bedsheets, pants, pajamas and undergarments. The backsheet 12 may thus comprise a woven or nonwoven material, polymeric films such as thermoplastic films of polyethylene or polypropylene, and/or composite materials such as a film-coated nonwoven material (i.e., having an inner film layer and an outer nonwoven layer). A suitable backsheet 12 is a polyethylene film having a thickness of from about 0.012 mm (0.5 mils) to about 0.051 mm (2.0 mils). Exemplary polyethylene films are manufactured by Clopay Corporation of Cincinnati, Ohio, under the designation BR-120 and BR-121 and by Tredegar Film Products of Terre Haute, Ind., under the designation XP-39385. The backsheet 12 is preferably embossed and/or matte-finished to provide a more clothlike appearance. Further, the backsheet 12 may permit vapors to escape from the absorbent core (i.e., the backsheet is breathable) while still preventing exudates from passing through the backsheet. The size of the backsheet 12 is dictated by the size of the absorbent core 18 and the exact absorbent article design selected.

The backsheet 12 and the topsheet 10 are positioned adjacent a garment facing surface and a wearing facing surface, respectively, of the absorbent core. The absorbent core 18 is preferably joined with the topsheet 10, the backsheet 12, or both in any manner as is known by attachment means such as those well known in the art. However, embodiments of the present invention are envisioned wherein portions of the entire absorbent core are unattached to one or both of the topsheet 10 and the backsheet 12.

For example, the backsheet 12 and/or the topsheet 10 may be secured to the absorbent core 18 or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258 or H-2031. The attachment means will preferably comprise an open pattern network of filaments of adhesive as is disclosed in U.S. Pat. No. 4,573, 986. An exemplary attachment means of an open pattern network of filaments comprises several lines of adhesive filaments swirled into a spiral pattern such as illustrated by the apparatus and method shown in U.S. Pat. Nos. 3,911,173, 4,785,996 and 4,842,666. Alternatively, the attachment means may comprise heat bonds, pressure bonds, ultrasonic bonds, dynamic mechanical bonds, or any other suitable attachment means or combinations of these attachment means as are known in the art.

The backsheet 12b preferably includes an inner and outer layer, each of which can be bonded to the other by a variety of means known in the art, including thermal bonds, adhesive bonds, ultrasonic lamination, or the like. Adhesive bonding can also be accomplished using adhesive slot coating, high frequency oscillation patterns, for example in swirl or spray patterns, and other fine denier and/or high coverage application techniques. Suitable laminate adhesives, which can be applied continuously or intermittently, can be obtained from Findley Adhesives, Inc. or from National Starch and Chemical Company.

The outer layer (or outer cover) of the backsheet can be made in a variety of forms using different processes. For example, the outer layer may be formed as a carded web, a bonded carded web, a spunbond web, a needled fabric, a woven fabric, or the like to provide a generally cloth-like texture to the wearer. Other additives such as titanium dioxide can represent about 0.5% or less, particularly about 0.3% or less, of the outer layer. In one particular embodiment, the outer layer comprises a spunbond web formed of about 99.5 to 100% polypropylene resin and about 0.5% or less other additives. The outer layer is desirably a lightweight material having a basis weight of about 15 to about 30 gsm and more preferably from about 15 to about 25 gsm.

The articles of the present invention additionally comprise one or more absorbent cores 18. The absorbent core 18 is at least partially disposed between the topsheet 10 and the backsheet 12 and may take on any size or shape that is compatible with the disposable absorbent article. Exemplary absorbent structures for use as the absorbent core of the present invention that have achieved wide acceptance and commercial success are described in U.S. Pat. Nos. 4,610,678, 4,673,402, and 4,888,231, and 4,834,735. The absorbent core may further comprise the dual core system containing an acquisition/distribution core of chemically stiffened fibers positioned over an absorbent storage core as detailed in U.S. Pat. Nos. 5,234,423 and 5,147,345.

In general, the absorbent core 18 is capable of absorbing or retaining liquids (e.g., menses, urine, and/or other body exudates). The absorbent core 18 is preferably compressible, conformable, and non-irritating to the wearer's skin. The absorbent core 18 may be manufactured in a wide variety of sizes and shapes (e.g., rectangular, oval, hourglass, "T" shaped, dog bone, asymmetric, etc.). The absorbent core 18 may include any of a wide variety of liquid-absorbent materials commonly used in absorbent articles, such as comminuted wood pulp, which is generally referred to as airfelt. Examples of other suitable absorbent materials for use in the absorbent core include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these.

As discussed herein "absorbent gelling materials" and "superabsorbent polymers" are those materials that, upon contact with aqueous fluids, such as bodily fluids, imbibes such fluids and form hydrogels. These absorbent gelling materials are typically capable of absorbing large quantities of aqueous bodily fluids, and further capable of retaining such absorbed fluids under moderate pressures. These absorbent gelling materials are typically in the form of discrete, nonfibrous particles. Other forms, such as fibers, foams, sheets, strips, or other macrostructures, are also suitable for use herein. Suitable absorbent gelling materials in the form of open cell foams may include those disclosed in U.S. Pat. Nos. 3,563,243, 4,554,297, 4,740,520, and 5,260,345.

The configuration and construction of the absorbent core 18 may also be varied (e.g., the absorbent core may have varying caliper zones and/or have a profile so as to be thicker in the center; hydrophilic gradients; superabsorbent gradients; or lower average density and lower average basis weight zones, e.g., acquisition zones; or may comprise one or more layers or structures). The total absorbent capacity of the absorbent core 18 should, however, be compatible with the design loading and the intended use of the absorbent article.

Further, the size and absorbent capacity of the absorbent core may be varied to accommodate different uses such as diapers, incontinence pads, pantiliners, regular sanitary napkins, and overnight sanitary napkins, and to accommodate wearers ranging from infants to adults. The absorbent core 18 can include other absorbent components that are often used in absorbent articles, for example, a dusting layer, a wicking or acquisition layer, or a secondary topsheet for increasing the wearer's comfort.

In certain embodiments of the present invention, the absorbent article may also include a sublayer disposed between the topsheet 10 and the backsheet 12. The sublayer may be any material or structure capable of accepting, storing or immobilizing bodily exudates. Thus, the sublayer may include a single material or a number of materials operatively associated with each other. Further, the sublayer may be integral with another element of the absorbent article or may be one or more separate elements joined directly or indirectly with one or more elements of the article. Further, the sublayer may include a structure that is separate from the core or may include or be part of at least a portion of the core.

Suitable materials for use as the sublayer may include large cell open foams, macro-porous compression resistant nonwoven highlofts, large size particulate forms of open and closed cell foams (macro and/or microporous), highloft nonwovens, polyolefin, polystyrene, polyurethane foams or particles, structures comprising a multiplicity of vertically oriented looped strands of fibers, absorbent core structures described above having punched holes or depressions, and the like. One embodiment of a sublayer includes a mechanical fastening loop landing element, having an uncompressed thickness of about 1.5 millimeters available as XPL-7124 from the 3M Corporation of Minneapolis, Minn. Another embodiment includes a 6 denier, crimped and resin-bonded nonwoven highloft having a basis weight of 110 grams per square meter and an uncompressed thickness of 7.9 millimeters which is available from the Glit Company of Wrens, Ga. Other suitable absorbent and nonabsorbent sublayers are described in U.S. Pat. Nos. 6,680,422 and 5,941,864. Further, the sublayer, or any portion thereof, may include or be coated with a lotion or other known substances to add, enhance or change the performance or other characteristics of the element.

Absorbent articles suitable for use as the present invention include diapers, training pants, incontinence products, diaper pants, disposable underwear, or the like. Suitable training pants and diaper pants can have seamed side portions or refastenable side portions. The present invention is particularly suited for use with training pants or diaper pants to aid in toilet training. Particular diapers and training pants suitable for use with the present invention are disclosed in U.S. Pat. Nos. 3,860,003, 4,636,207, 4,695,278, 4,704,115, 4,795,454, 4,900,317, 4,909,803 (Reissued as USRE34920), 5,085,654, 5,492,751, 6,476,288, 6,627,787, 5,507,760, 5,609,587, 5,635,191, 5,643,588, 6,118,041, SIR H1630, 5,246,433, 5,769,838, 5,899,895, 5,899,896, and 6,120,487. Additional patents discussing suitable training pants are disclosed earlier herein.

The article of the present invention may also comprise an elastic waist feature that provides improved fit and containment; and a fastening system which forms a side closure which maintains the first waist region and the second waist region in an overlapping configuration such that lateral tensions are maintained around the circumference of the absorbent article to maintain the absorbent article on the wearer. The absorbent article may also comprise elasticized side panels (not shown) in the waist regions and to provide an elastically extensible feature that provides a more comfortable and contouring fit and more effective application of the absorbent article. In certain embodiments, the elasticized side panels are positioned such that a front and rear side panel are joined to one another along their longitudinal edges. This joining along the longitudinal edges of the panels may be permanent or refastenable. For permanent joints, the panels may be adhered to one another via ultrasonic bonding, high tack, adhesives, etc. For refastenable joints, the panels may be joined via hook and loop fasters, mild co-adhesive materials, low tack adhesives, etc.

Low Basis Weight, Low Glue Burn Through Films

The films of the present invention have a basis weight of less than about 16 gsm, less than about 15 gsm, less than about 14 gsm, less than about 13 gsm, less than about 12 gsm, less than about 11 gsm, less than about 10 gsm, less than about 8 gsm, less than about 6 gsm.

In order to achieve low glue burn through, the films of the present invention may comprise polypropylene. Without being limited by theory, polypropylene usually melts at temperatures in the range of from about 150° C. to about 160° C. Polyethylene, which is typically used in films for absorbent articles, generally melts at temperatures in the range of from about 100° C. to about 130° C. Films comprising both polyethylene and polypropylene exhibit more heat resistance than polyethylene alone, thus less glue burn through occurs.

The present invention is directed to films comprising polymeric resins comprising both polyethylene and polypropylene and/or only polypropylene. Such films comprise polymeric resins comprising at least about 10% polypropylene, at least about 20% polypropylene, at least about 30% polypropylene, at least about 40% polypropylene, at least about 50% polypropylene, at least about 60% polypropylene, at least about 70% polypropylene, at least about 80% polypropylene, at least about 90% polypropylene.

Films suitable for the present invention may be breathable films. Breathable films are polymeric films containing filler stretched to contain internal microporosities. Breathable films are described in U.S. Pat. No. 4,472,328

Films suitable for the present invention may be coextruded. Coextruded films are formed by the process of extruding two or more materials through a single die with two or more orifices arranged so that the extrudates merge and weld together into a laminar structure before chilling. Each material is fed to the die from a separate extruder, but the orifices may be arranged so that each extruder supplies two or more plies of the same material. Coextrusion can be employed in film blowing, free film extrusion, and extrusion coating processes. The advantage of coextrusion is that each ply of the laminate imparts a desired characteristic property, such as stiffness, heat-sealability, impermeability or resistance to some environment, all of which properties would be impossible to attain with any single material.

According to the present invention, a model was created to predict glue burn through using heat transfer principles. This model for determining glue burn through involves measuring the thermal conductivity and thermal effusivity of the film. Thermal conductivity is a physical property that characterizes a substance's ability to transfer heat. The thermal conductivity differs with each substance's structure, density, humidity, pressure, and temperature. Materials having a large thermal conductivity value are good conductors of heat and those with small values are good insulators. Thermal effusivity is the property that dictates the interfacial temperature when two semi-infinite objects at different temperatures touch one another. After incorporating the thermal properties into the model, a predictive glue burn through value is achieved reflecting present conditions of the film.

The ratio below describes the ability of the polymer barrier film to resist glue burn through. In this model, glue burn through is correlated to heat capacity×density.

$$GBT = Cp\rho = (\text{effusivity})^2/\kappa$$

Wherein:
Cp=heat capacity, J/kg-Kelvin
κ=Thermal Conductivity, watt/meter-Kelvin
ρ=density, g/cc or kg/cubic meter
Thermal Effusivity units are watt-second$^{0.5}$/meter 2-Kelvin The model predicts that a heat capacity×density value of greater than about 970,000 Ws/m$^3$K, greater than about 1,000,000 Ws/m$^3$K, greater than about 1,050,000 Ws/m$^3$K, 1,100,000 Ws/m$^3$K, 1,200,000 Ws/m$^3$K is indicative of a film having low glue burn through. The model predicts that a heat capacity×density value of less than about 970,000 Ws/m$^3$K shows visible glue burn through. Calculating the glue burn through is accomplished by measuring the thermal effusivity and thermal conductivity of the polymer barrier film.

Thermal Conductivity and Thermal Effusivity Test Method

Thermal conductivity and thermal effusivity measurements for solid materials may be obtained by sending samples to Mathis Instruments at 21 Alison Blvd. in Fredericton, Nebr. There, a Mathis TC-01™ Thermal Conductivity Analyzer is used to make the calculations. The method is known as the Modified Hot Wire technique. This method requires a number of 7.62 centimeter square plies such that at least 1 millimeter of thickness under a weight of 652 grams over an area of 250 square millimeters will be achieved. The material used for the sample should be equilibrated for at least 2 hours at a temperature of 23 degrees C. (+/−2 degree C.) and 50% (+/−2%) relative humidity. The machine direction of each ply should be noted and all should be placed in the same orientation, such orientation should be parallel with the axis of the longer dimension of the machine's sensor. The method employed is to be consistent with the principles of operation for the Mathis TC-01.

In the case of testing a polymer barrier film that is contained in an article, the film must be removed from the article and the film's surfaces cleaned of any contaminating materials such as glue, fiber, etc. It is helpful if the entire sheet of barrier film is removed from an article so that the contaminants can be removed with as little damage as possible to the film. The pieces of film can then be marked for orientation and cut to uniform size approximately at least 10 centimeters square. These pieces can then be gently treated with a solvent that will dissolve the hot melt adhesives while not causing damage or swelling to the film. Suitable solvents include, but are not limited to methylene chloride or acetone. The available plies of film should then be carefully stacked on top of each other with all pieces oriented in the same direction. The stack of plies should then be conditioned and rolled with a hard rubber or steel roller of similar width to that of the plies weighing 2 kg to 4 kg to press out the excess air or pockets of air between the plies. The sample, if it meets the above thickness requirement and is then cut to 7.62 centimeters on each side, is then ready to be tested.

The test procedures conducted at Mathis Instruments includes the following steps:
Place a 652 g weight on the top of the at least 1 mm thick sample to optimize sample contact with the spring-loaded sensor.
Permit the sample sufficient time to stabilize to iso-thermal conditions with the environment and sensor.

Place the sample and sensor inside an environmental chamber for testing at elevated temperature.

Set up the instrument using the following parameters: a 10-second test time, 4-second start time and 5-minute cooling interval.

For each sample received, three thermal conductivity measurements are performed at 50° C. using the auto test mode.

For each sample received, three thermal effusivity measurements are performed at 50° C. using the auto test mode.

Report the average of the 3 readings for each property.

The thermal conductivity and thermal effusivity measurements are then included in the aforementioned equation to predict the glue burn through value via the heat capacity× density equation.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising a polymeric film having a heat capacity×density value of greater than 970,000 $Ws/m^3K$ as measured in the method described herein, said film having a basis weight of less than about 8 gsm, said film comprising a polymeric resin that comprises at least 10% of polypropylene, wherein said film is a breathable film; wherein said polymeric film is coextruded with a second material; wherein said absorbent article is a diaper.

2. The polymeric film of claim 1, wherein said polymeric resin comprises at least 20% of polypropylene.

3. The polymeric film of claim 1, wherein said polymeric resin comprises at least 30% of polypropylene.

4. The polymeric film of claim 1, wherein said polymeric resin comprises at least 50% of polypropylene.

5. The polymeric film of claim 1, wherein said polymeric resin comprises at least 70% of polypropylene.

6. The polymeric film of claim 1, wherein said polymeric resin comprises at least 90% of polypropylene.

* * * * *